United States Patent
Isogai

(10) Patent No.: US 7,128,417 B2
(45) Date of Patent: Oct. 31, 2006

(54) REFRACTIVE POWER MEASUREMENT APPARATUS

(75) Inventor: Naoki Isogai, Nishio (JP)

(73) Assignee: Nidek Co., Ltd. (JP)

( * ) Notice: Subject to any disclaimer, the term of this patent is extended or adjusted under 35 U.S.C. 154(b) by 546 days.

(21) Appl. No.: 10/603,697

(22) Filed: Jun. 26, 2003

(65) Prior Publication Data
US 2004/0061832 A1    Apr. 1, 2004

(30) Foreign Application Priority Data
Jun. 28, 2002   (JP) ............................. 2002-190737

(51) Int. Cl.
*A61B 3/10* (2006.01)
(52) U.S. Cl. ................. 351/206; 351/211; 351/212
(58) Field of Classification Search ............ 351/206, 351/207, 208, 209, 210, 216, 217, 233, 234, 351/235, 236
See application file for complete search history.

(56) References Cited

U.S. PATENT DOCUMENTS 5,270,749 A * 12/1993 Okumura .................. 351/211
5,309,186 A *  5/1994 Mizuno .................... 351/212
5,500,697 A    3/1996 Fujieda
5,767,940 A *  6/1998 Hayashi et al. ............ 351/205

FOREIGN PATENT DOCUMENTS

| JP | 1-293841 A1 | 11/1989 |
| JP | 2-252437-1 | 10/1990 |
| JP | 10-305013 A1 | 11/1998 |

* cited by examiner

*Primary Examiner*—Nini F. Legesse
(74) *Attorney, Agent, or Firm*—Rader Fishman & Grauer; Ronald P. Kananen

(57) ABSTRACT

A refractive power measurement apparatus capable of measuring a refractive power of an optical system to be measured with a simple constitution at low cost. The refractive power measurement apparatus includes a projection optical system which projects measurement light onto an optical system to be measured, a photo-receiving optical system provided with a photodetector which photo-receives the measurement light from the optical system to be measured and a lens system which guides the measurement light onto the photodetector, a moving device for moving the lens system within a plane intersecting at right angles with an optical axis of the photo-receiving optical system so as to form a predetermined measurement pattern image on a photo-receiving surface of the photodetector, and a calculation device for calculating a refractive power of the optical system to be measured based on the measurement pattern image.

8 Claims, 5 Drawing Sheets

REFRACTIVE POWER MEASUREMENT APPARATUS

BACKGROUND OF THE INVENTION

1. Field of the Invention

The present invention relates to a refractive power measurement apparatus which measures a refractive power of an optical system of an eye, a spectacle lens or the like.

2. Description of Related Art

Conventionally, there is known a refractive power measurement apparatus which projects spot light onto a fundus via a central portion of a pupil, places a ring-shaped opening or a mask pattern which is symmetric with respect to an optical axis of a photo-receiving optical system, and a lens, so as to derive reflection light from the fundus through the periphery of the pupil to guide the reflection light onto a photodetector, and measures a refractive power of an eye based on a measurement pattern image formed on a photo-receiving surface of the photodetector. For example, Japanese Patent Application Unexamined Publication No. Hei1-293841 discloses that the measurement pattern image is formed on the photo-receiving surface of the photodetector using a ring-shaped diaphragm (a ringshaped iris) and a ring-shaped lens. Japanese Patent Application Unexamined Publication No. Hei2-252437 discloses that the measurement pattern image is formed on the photo-receiving surface of the photodetector using a diaphragm with a hole (a perforation iris), a lens and a wedge prism. Additionally, Japanese Patent Application Unexamined Publication No. Hei10-305013 (corresponding to U.S. Pat. No. 6,234,978 and U.S. Pat. No. 6,540,692) discloses that the measurement pattern image is formed on the photo-receiving surface of the photodetector using a plurality of micro-Fresnel lenses arranged within a plane intersecting at right angles with an optical axis.

However, in the case of utilizing the ring-shaped lens or the plurality of micro-Fresnel lenses, a fine processing technique different from a usual one is required. Therefore, there are problems of an increase in cost and difficulty in design. Further, also in the case of utilizing the wedge prism, it is difficult to process the wedge prism, and moreover, it is required to mount the wedge prism at a predetermined position with accuracy. Therefore, the structure becomes complicated and incurs much cost.

SUMMARY OF THE INVENTION

An object of the invention is to overcome the problems described above and to provide a refractive power measurement apparatus capable of measuring a refractive power of an optical system to be measured with a simple constitution at low cost.

To achieve the objects and in accordance with the purpose of the present invention, a refractive power measurement apparatus has a projection optical system which projects measurement light onto an optical system to be measured, a photo-receiving optical system provided with a photodetector which photo-receives the measurement light from the optical system to be measured and a lens system which guides the measurement light onto the photodetector, moving means for moving the lens system within a plane intersecting at right angles with an optical axis of the photo-receiving optical system so as to form a predetermined measurement pattern image on a photo-receiving surface of the photodetector, and calculation means for calculating a refractive power of the optical system to be measured based on the measurement pattern image.

In another aspect of the present invention, a refractive power measurement apparatus has a projection optical system which projects spot-shaped measurement light onto a fundus via a central portion of a pupil of an eye, a photo-receiving optical system provided with a photodetector which photo-receives the measurement light from the fundus and a lens system which guides the measurement light onto the photodetector, moving means for moving the lens system within a plane intersecting at right angles with an optical axis of the photo-receiving optical system so as to form a predetermined measurement pattern image on a photo-receiving surface of the photodetector, and calculation means for calculating the refractive power of the eye based on the measurement pattern image, wherein the lens system is arranged at a position conjugate with a position of the pupil, and the photodetector is arranged in the vicinity of a focal point of the lens system.

Yet, in another aspect of the present invention, a refractive power measurement apparatus further has a projection optical system which projects parallel measurement light onto a lens, a photo-receiving optical system provided with a photodetector which photo-receives the measurement light passed through the lens and a lens system which guides the measurement light onto the photodetector, moving means for moving the lens system within a plane intersecting at right angles with an optical axis of the photo-receiving optical system so as to form a predetermined measurement pattern image on a photo-receiving surface of the photodetector, and calculation means for calculating the refractive power of the lens based on the measurement pattern image, wherein the lens system is arranged between the lens and the photodetector, and the photodetector is arranged in the vicinity of a focal point of the lens system.

Additional objects and advantages of the invention are set forth in the description which follows, are obvious from the description, or may be learned by practicing the invention. The objects and advantages of the invention may be realized and attained by the refractive power measurement apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
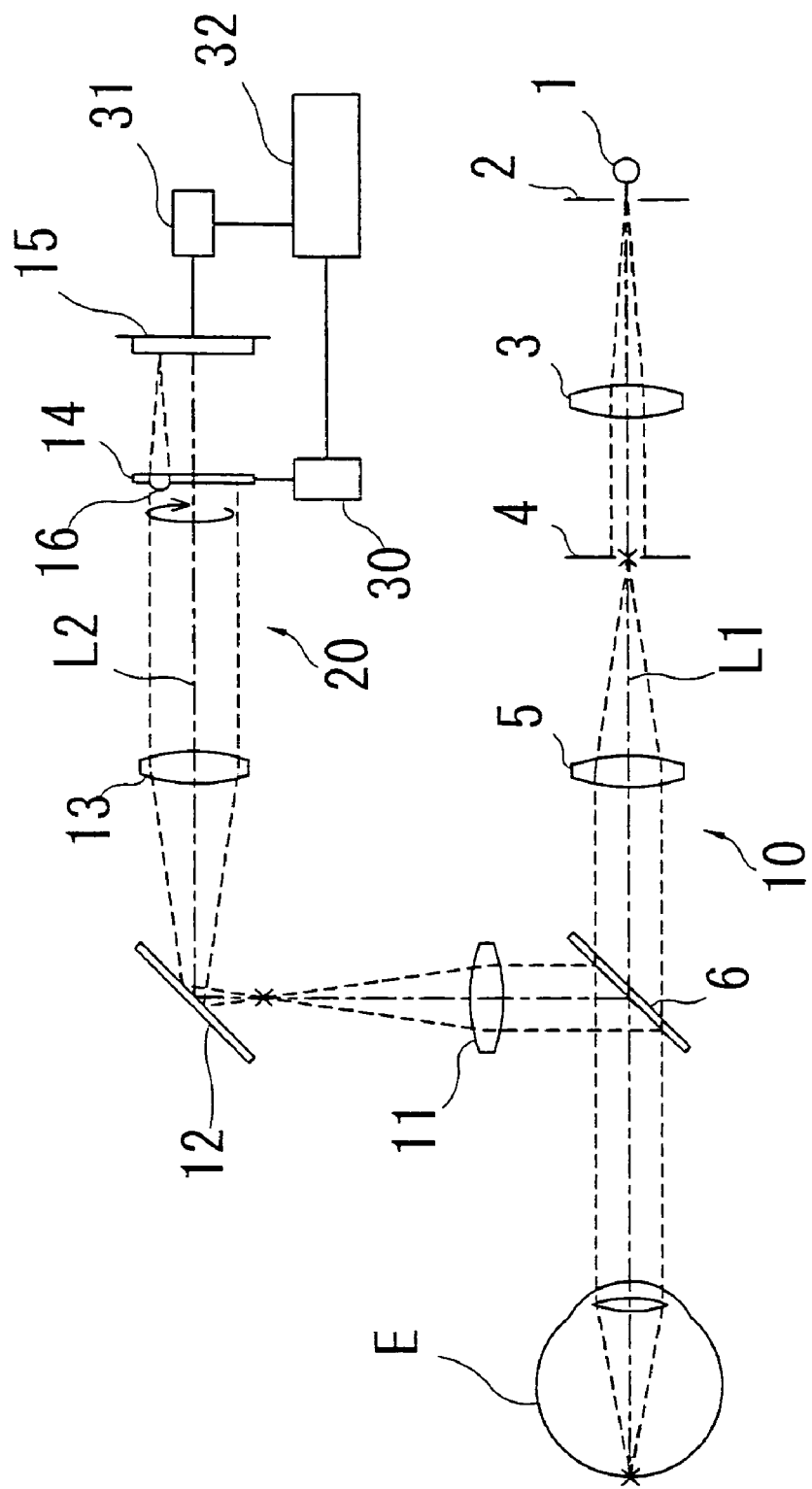
FIG. 1 is a view showing a schematic configuration of an optical system and a control system included in an eye refractive power measurement apparatus consistent with one preferred embodiment of the present invention.

A detailed description of one preferred embodiment of a refractive power measurement apparatus embodied by the present invention is provided below with reference to the accompanying drawings. FIG. 1 is a view showing a schematic configuration of an optical system and a control system included in an eye refractive power measurement apparatus consistent with one preferred embodiment of the present invention.

A projection optical system 10 projects measurement light onto an eye E to be measured. Arranged on an optical axis L1 of the projection optical system 10 are a light source 1 which emits infrared measurement light, a diaphragm 2 having a small opening, a collimator lens 3, a diaphragm 4 having a small opening as with the diaphragm 2, an objective lens 5, and a half mirror 6. The diaphragm 2 is arranged at a position conjugate with a pupil of the eye E via the lenses 3 and 5. Additionally, the diaphragm 4 is arranged at a position conjugate with an emmetropic fundus of the eye E via the lens 5. Incidentally, an LED emitting infrared light is employed for the light source 1 in this embodiment; however, the present invention is not limited thereto. An SLD (super luminescent diode) and the like may also be employed for the light source 1.

The measurement light emitted from the light source 1 passes through the diaphragm 2, and then is made into parallel light by the lens 3 to illuminate the diaphragm 4. The measurement light via the diaphragm 4 passes through the lens 5 and the half mirror 6, and then through a central portion of the pupil of the eye E to project the measurement light in a spot shape onto the fundus of the eye E.

A photo-receiving optical system 20 photo-receives the measurement light reflected from the eye E. Arranged on an optical axis L2 of the photo-receiving optical system 20 are an objective lens 11, a reflection mirror 12, a collimator lens 13, a rotation member 14 with a small lens 16 mounted thereon, and a photodetector 15 having a sensitivity to an infrared range. An existent two-dimensional area sensor such as a CCD is employed for the photodetector 15. The rotation member 14 (the small lens 16) is arranged at a position conjugate with the pupil of the eye E via the lenses 11 and 13. In addition, the plane of the rotation member 14 is arranged to intersect at right angles with the optical axis L2. Besides, the photodetector 15 is placed in the vicinity of a focal point of the small lens 16 to have a position optically conjugate with the emmetropic fundus of the eye E.

Driving means 30 rotates the rotation member 14 about the optical axis L2. Incidentally, a DC motor is employed for the driving means 30 in this embodiment; however, the present invention is not limited thereto. A pulse motor or the like may also be employed for the driving means 30. The rotation member 14 is rotated by the driving means 30 at such a rate that the rotation member 14 is rotated once or more within a photo-receiving time for one frame (or one field) of the photodetector 15. Incidentally, if the photodetector 15 of which the photo-receiving time is variable is employed, measurement can be performed with rapidity by shortening the photo-receiving time and increasing the rate of rotation by the driving means 30 accordingly owing to this, the measurement becomes little influenced by movement, blink or the like of the eye E, or unsteadiness of a hand in the case of a hand-held type apparatus. Besides, if the light reflected from the fundus is weak, measures may be taken by lengthening the photo-receiving time of the photodetector 15.

Reference numeral 31 is calculation means, and 32 is control means. The calculation means 31 calculates a refractive power (a spherical power, an astigmatic power, and an axial angle) based on information from the photodetector 15. Further, the control means 32 controls the driving means 30 or other elements included in the eye refractive power measurement apparatus.

Figure 2:
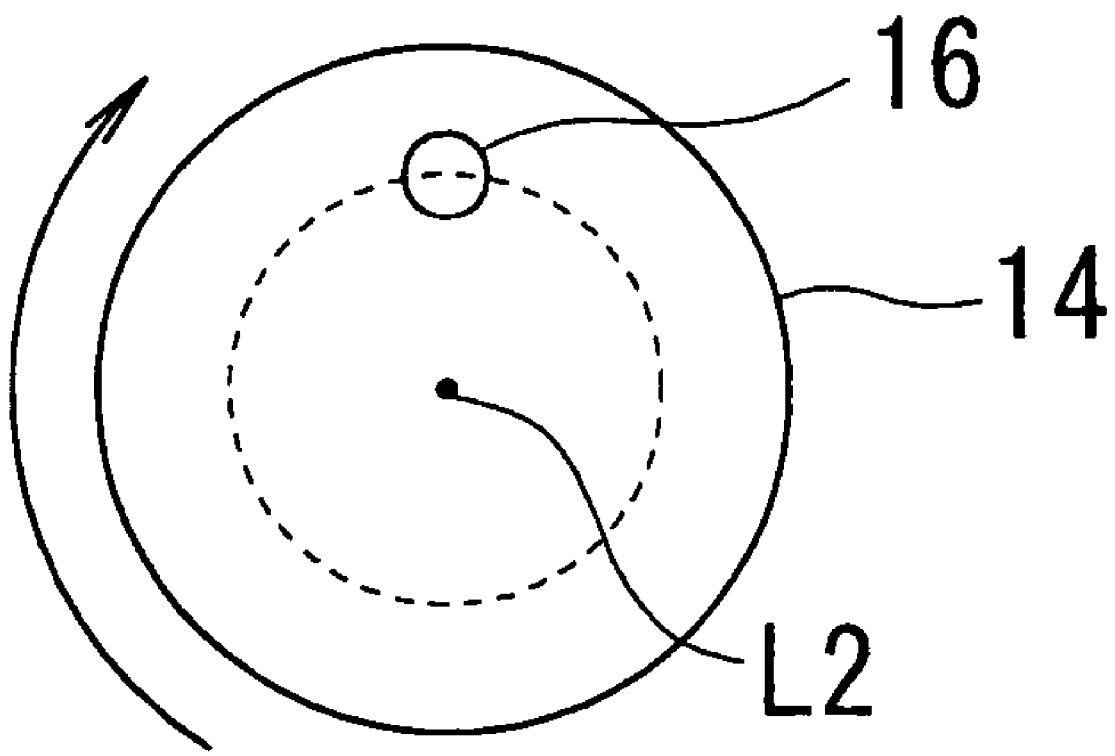
FIG. 2 is a detailed view of a rotation member.

FIG. 2 is a detailed view of the rotation member 14 being a lightproof plate in a disk shape. The small lens 16 is mounted on the rotation member 14 at a position a predetermined distance away (deviated) from the center of the rotation member 14 (the optical axis L2). In addition, the small lens 16 is mounted so that its optical axis intersects at right angles with the plane of the rotation member 14 (parallel to the optical axis L2). The rotation member 14 disposed on the optical axis L2 is rotated, and the small lens 16 is rotated about the optical axis L2 on a plane which intersects at right angles with the optical axis L2.

The measurement light reflected from the fundus of the eye E is reflected off the half mirror 6, and forms an intermediate image by means of the lens 11. Further, the measurement light is reflected off the mirror 12 and is made into parallel light by the lens 13 (in a case where the eye E is emmetropia), and then passes through the small lens 16 mounted on the rotation member 14 to form an image on a photo-receiving surface of the photodetector 15. At the time of the measurement, the small lens 16 is rotated in agreement with the rotation member 14. Therefore, the light through the lens 16 forms a ring-shaped image on the photo-receiving surface of the photodetector 15 as a measurement pattern image. Incidentally, the rotation member 14 may be rotated only as occasion arises such as when measurement is performed, or may be continuously rotated while the apparatus has power applied to it.

Figure 3A:
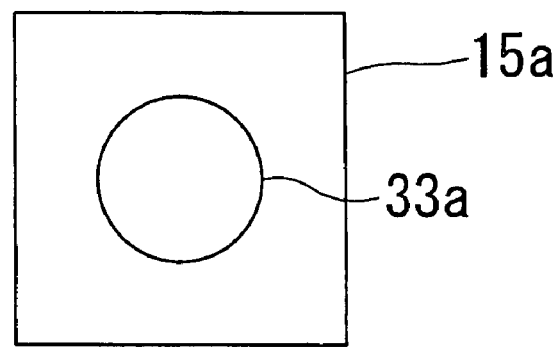
FIGS. 3A to 3C are views showing a state of variation in a ring image formed on a photo-receiving surface of a photodetector.
Figure 3B:
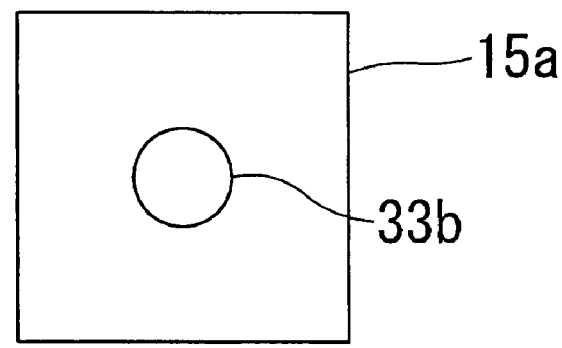
Figure 3C:
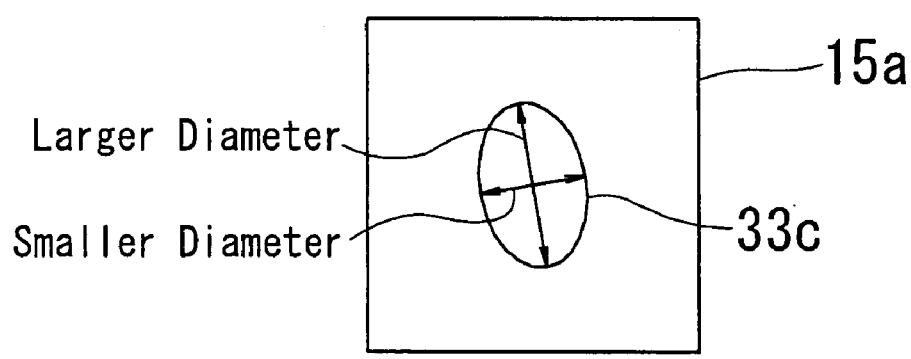

FIGS. 3A to 3C are views showing a state of variation in the ring image formed on the photo-receiving surface 15a of the photodetector 15. FIG. 3A shows a case where the eye E is emmetropia, and a ring image 33a in a predetermined size is formed therein. FIG. 3B shows a case where the eye E is myopia, and a ring image 33b smaller than the ring image 33a is formed therein. If the eye E is hypermetropia, a ring image larger than the ring image 33a is formed. FIG. 3C shows a case where the eye E is astigmatism, and a ring image 33c in an oval shape is formed therein.

According to the shape of the ring image formed on the photodetector 15, the calculation means 31 calculates the refractive power of the eye E. The spherical power is obtained according to the size of a diameter of the ring image as the size of the ring image with the emmetropic eye shown in FIG. 3A is taken as 0 diopter. Further, the astigmatic power is obtained from the ratio between a larger diameter and a smaller diameter of the oval ring image as shown in FIG. 3C, and the axial angle is obtained from the inclination of the oval ring image. The control means 32 outputs values of the refractive power obtained to a monitor and a printer which are not illustrated.

Incidentally, if the refractive power of the eye E is far from that of an emmetropic eye, an obscure image is possibly formed on the photodetector 15. In this case, a part of optical members arranged within the photo-receiving optical system 20 may be moved in the direction of the optical axis L2 to adjust a state of the image formed on the photo-receiving surface of the photodetector 15. For example, the lens 13, the rotation member 14 and the photodetector 15 may be integrally moved in the direction of the optical axis L2, so that the image is clearly formed on the photo-receiving surface of the photodetector 15. Besides, when a diaphragm is arranged at a position conjugate with the fundus, the measurement light other than the light reflected from the fundus is cut off to improve measurement accuracy. In addition, it is better if the diaphragm may be movable in the direction of the optical axis L2.

As described above, in this embodiment, the small lens 16 mounted on the rotation member 14 is rotated, and the ring image being the measurement pattern image may be formed on the photo-receiving surface of the photodetector 15. Owing to this, accurate measurement may be performed with a simple constitution at lower cost than that in the case of using the conventional ring-shaped lens, the wedge prism or the like.

Incidentally, if a normal measurement pattern image cannot be detected (photo-received) due to the existence of irregular reflection light (e.g. diffused light caused by cataract, an eyelid, eyelash or the like) in the first measurement, the irregular reflection light may be eliminated in the second measurement by switching off the light source 1 (or cutting off the measurement light using a shutter) in a range of a rotation angle of the rotation member 14, in which range the normal measurement pattern image cannot be detected. In this case, the measurement pattern image comes in a discontinuous shape (e.g. an arc shape); however, an approximation of a whole shape and the like enable obtaining a refractive power and the like. Thus, when the light source 4 is switched off (or the measurement light is cut off) only in a certain range of the rotation angle using the control means 32, a pulse motor or the like capable of detecting a rotation angle may be employed as the driving means 30.

Figure 4:
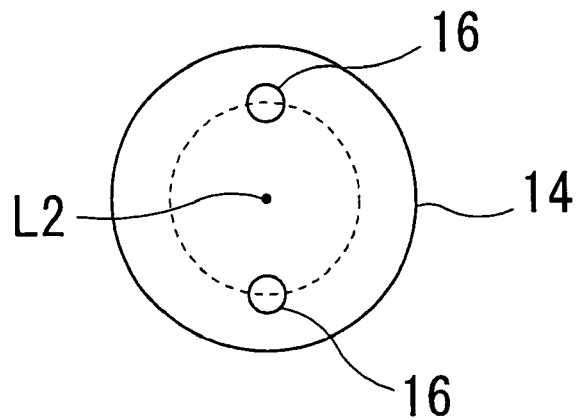
FIG. 4 is a view showing a modified embodiment of the rotation member.
Figure 5:
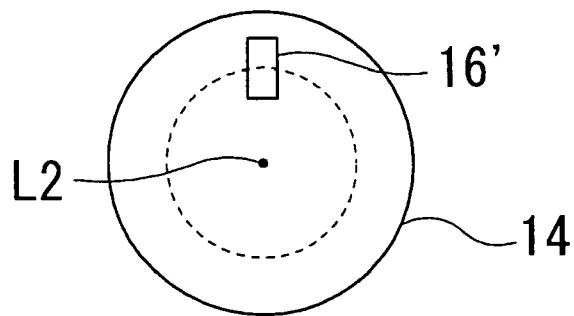
FIG. 5 is a view showing another modified embodiment of the rotation member.

Besides, in FIG. 2, one small lens 16 is mounted on the rotation member 14; however, the present invention is not limited thereto. For example, as shown in FIG. 4, if two or more small lenses 16 are mounted on a concentric circle having a rotation axis of the rotation member 14 (the optical axis L2) as its center (at positions same distances from the optical axis L2), a ring image being a measurement pattern image may be obtained in shorter time. Further, a small lens in another shape may be employed instead of the small lens 16 in a circular shape. For example, as shown in FIG. 5, if a cylindrical lens 16' longer than the diameter of the small lens 16 is used, a thick ring image is obtained as a measurement pattern image. The thick ring image as a measurement pattern image may help obtaining an averaged refractive power in a wider region of the eye E. Furthermore, each edge of the outer diameter and the inner diameter in the thick ring image may be used to obtain refractive powers for two kinds of diameters.

Figure 6:
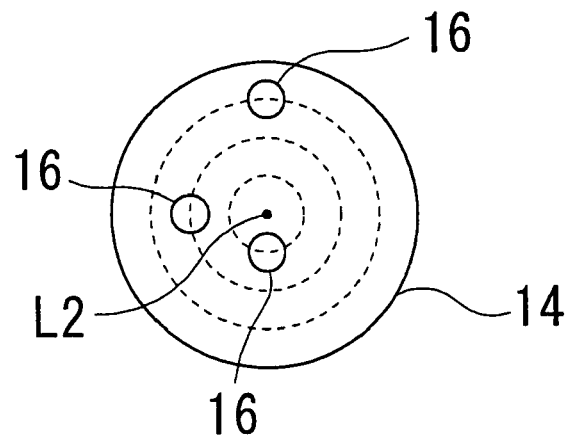
FIG. 6 is a view showing still another modified embodiment of the rotation member.

In addition, as shown in FIG. 6, a plurality of the small lenses 16 may be arranged on different concentric circles having the rotation axis of the rotation member 14 (the optical axis L2) as their center (at positions different distances from the optical axis L2) to obtain a plurality of separate ring images (measurement pattern images). By utilizing the plurality of measurement pattern images, a refractive power in a wide range of the pupil of the eye E may be obtained, and a refractive power map may be prepared.

Furthermore, in this embodiment, the rotation member 14 rotates about the optical axis L2; however, the present invention is not limited thereto. For example, the rotation member 14 may be two-dimensionally moved on the plane intersecting at right angles with the optical axis L2 by another driving means while the rotation member 14 is rotated to change a measurement portion of the eye E.

In addition, in the aforementioned embodiment, the rotation member 14 is rotated to obtain the ring-shaped measurement pattern image; however, the present invention is not limited thereto. For example, a measurement pattern image may be obtained not by rotating the rotation member 14 but by moving it so as to make a rectangular locus on the plane intersecting at right angles with the optical axis L2. Further, assume that four lenses 16 are uniformly arranged on concentric circles having the rotation axis of the rotation member 14 as their center to obtain a refractive power and the like from four point images formed by the four lenses 16, and measurement at an arbitrary position may be performed by rotating and moving the four point images. In that method, opaque parts due to cataract and the like may be eliminated from the measurement. Furthermore, even if the rotation member 14 is continuously rotated, a point image may be formed at a position (range) with an arbitrary rotation angle by lighting the light source 1 at a predetermined rotation angle in infinitesimal time. According to that method, a change in the refractive power of the eye E may be obtained at points.

As stated above, it is essential for the shape of the measurement pattern image only that at least three meridians which pass the optical axis L2 on the photo-receiving surface of the photodetector 15 may be obtained, or that the refractive power of the eye E may be obtained by shape variation of the measurement pattern image detected (photo-received).

In addition, in this embodiment, an explanation is made with the eye refractive power measurement apparatus as an example; however, the present invention is not limited thereto. For example, the present invention may be applied to a lens meter which measures a refractive power of a spectacle lens and the like.

Figure 7:
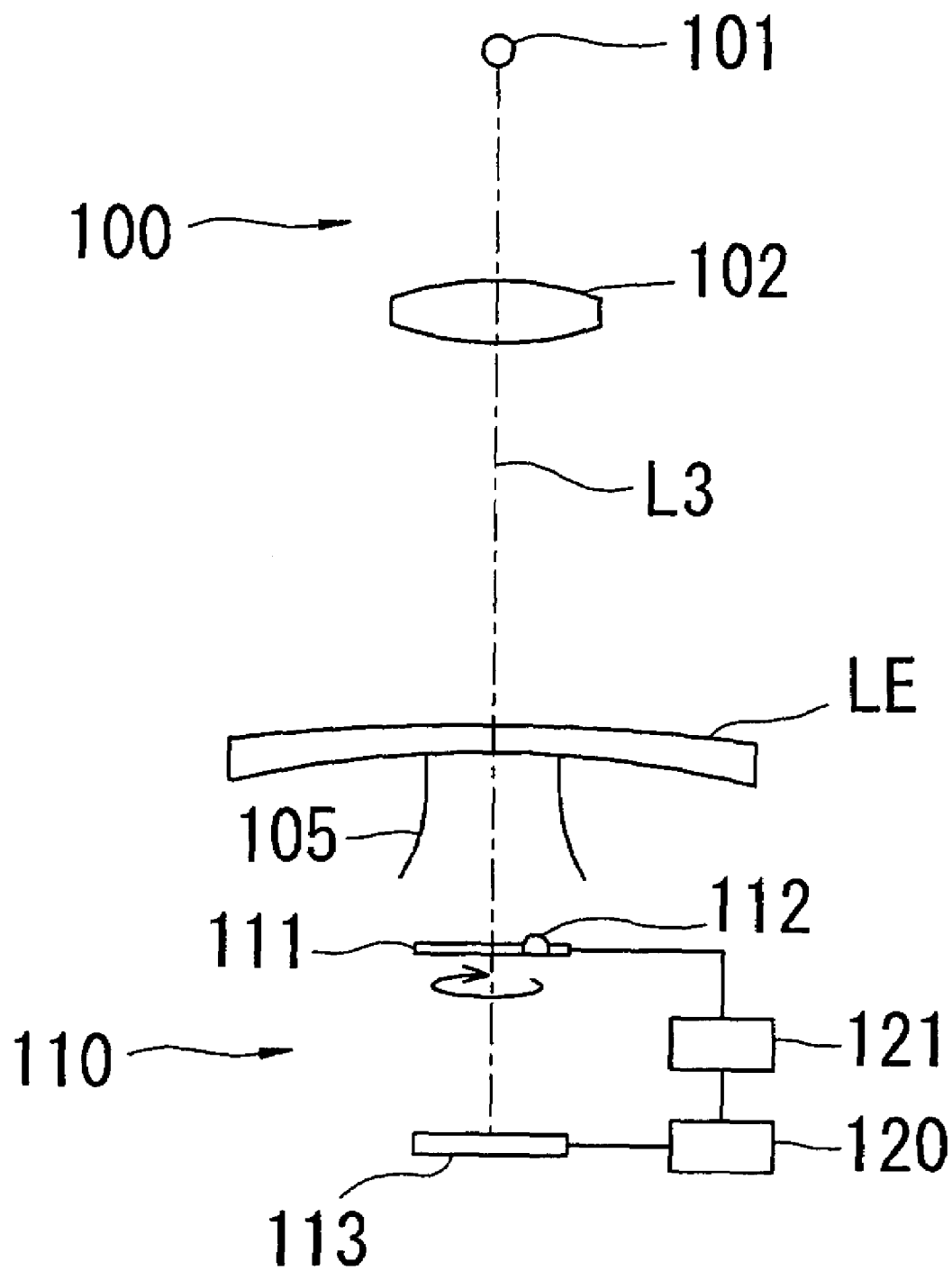
FIG. 7 is a view showing a schematic configuration of an optical system and a control system included in a lens meter consistent with another preferred embodiment of the present invention.

FIG. 7 is a view showing a schematic configuration of an optical system and a control system included in a lens meter consistent with another preferred embodiment of the present invention. A projection optical system 100 projects measurement light onto a lens LE to be measured. Arranged on an optical axis L3 of the projection optical system 100 are a light source 101 which emits the measurement light, and a collimator lens 102 which makes the measurement light into parallel light. The lens LE is disposed on a nosepiece 105 having an opening through which the optical axis L3 passes. The measurement light passed through the lens LE is guided onto a photodetector 113 via a small lens 112 of a photo-receiving optical system 110. The small lens 112 is mounted at a position a predetermined distance away (deviated) from the center of a rotation member 111 (the optical axis L3). Further, the small lens 112 is mounted on the rotation member 111 so that its optical axis intersects at right angles with the plane of the rotation member 111 (parallel to the optical axis L3). When the rotation member 111 is rotated by driving means 121, the small lens 112 is rotated about the optical axis L3 on a plane which intersects at right angles with the optical axis L3. Incidentally, the photodetector 113 is arranged in the vicinity of a focal point of the small lens 112. Control means 120 obtains a refractive power of the lens LE from a ring-shaped measurement pattern image photo-received on the photodetector 113. Likewise, in the case of the lens meter, as is the case with the above-mentioned constitution, various modifications may be made such that a plurality of small lenses 112, a plurality of ring-shaped measurement pattern images, or the like are employed.

As mentioned above, according to the present invention, a refractive power may be accurately measured with a simple constitution at lower cost.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A refractive power measurement apparatus comprising:
   a projection optical system which projects measurement light onto an optical system to be measured;
   a photo-receiving optical system provided with a photodetector which photo-receives the measurement light from the optical system to be measured and a lens system which guides the measurement light onto the photodetector;
   moving means for moving the lens system within a plane intersecting at right angles with an optical axis of the photo-receiving optical system so as to form a predetermined measurement pattern image on a photo-receiving surface of the photodetector; and
   calculation means for calculating a refractive power of the optical system to be measured based on the measurement pattern image,
   wherein the lens system is arranged at a position deviated from the optical axis of the photo-receiving optical system; and
   the moving means includes rotation means for rotating the lens system about the optical axis of the photo-receiving optical system.

2. The refractive power measurement apparatus according to claim 1, wherein the rotation means rotates the lens system at least once within a photo-receiving time of the photodetector so as to form a ring-shaped measurement pattern image.

3. The refractive power measurement apparatus according to claim 2, wherein the photo-receiving time of the photodetector is variable.

4. The refractive power measurement apparatus according to claim 1, wherein the lens system is arranged at a plurality of positions, respectively, each of the plurality of positions being placed at a same distance from the optical axis of the photo-receiving optical system.

5. The refractive power measurement apparatus according to claim 1, wherein the lens system is arranged at a plurality of positions, respectively, each of the plurality of positions being placed at a different distance from the optical axis of the photo-receiving optical system.

6. The refractive power measurement apparatus according to claim 1, further comprising:
   detecting means for detecting an rotation angle of the lens system; and
   control means for controlling projection of the measurement light based on a result of detection obtained by the detecting means.

7. A refractive power measurement apparatus for measuring a refractive power of an eye to be measured, the apparatus comprising:
   a projection optical system which projects spot-shaped measurement light onto a fundus via a central portion of a pupil of the eye;
   a photo-receiving optical system provided with a photodetector which photo-receives the measurement light from the fundus and a lens system which guides the measurement light onto the photodetector;
   moving means for moving the lens system within a plane intersecting at right angles with an optical axis of the photo-receiving optical system so as to form a predetermined measurement pattern image on a photo-receiving surface of the photodetector; and
   calculation means for calculating the refractive power of the eye based on the measurement pattern image.
   wherein the lens system is arranged at a position conjugate with a position of the pupil, and the photodetector is arranged in the vicinity of a focal point of the lens system,
   wherein the lens system is arranged at a position deviated from the optical axis of the photo-receiving optical system, and
   the moving means includes rotation means for rotating the lens system about the optical axis of the photo-receiving optical system.

8. A refractive power measurement apparatus for measuring a refractive power of a lens to be measured, the apparatus comprising:
   a protection optical system which projects measurement light onto the lens;
   a photo-receiving optical system provided with a photodetector which photo-receives the measurement light passed through the lens and a lens system which guides the measurement light onto the photodetector;
   moving means for moving the lens system within a plane intersecting at right angles with an optical axis of the photo-receiving optical system so as to form a predetermined measurement pattern image on a photo-receiving surface of the photodetector; and
   calculation means for calculating the refractive power of the lens based on the measurement pattern image,
   wherein the lens system is arranged between the lens and the photodetector, and the photodetector is arranged in the vicinity of a focal point of the lens system,
   wherein the lens system is arranged at a position deviated from the optical axis of the photo-receiving optical system, and
   the moving means includes rotation means for rotating the lens system about the optical axis of the photo-receiving optical system.

* * * * *